United States Patent
Frey et al.

(10) Patent No.: US 10,507,435 B1
(45) Date of Patent: Dec. 17, 2019

(54) MEMBRANE PROCESS FOR OLEFIN SEPARATION

(71) Applicant: UOP LLC, Des Plaines, IL (US)

(72) Inventors: Stanley J. Frey, Palatine, IL (US); J. Mark Houdek, Bartlett, IL (US); Chunqing Liu, Arlington Heights, IL (US); Trung Pham, Mount Prospect, IL (US)

( * ) Notice: Subject to any disclaimer, the term of this patent is extended or adjusted under 35 U.S.C. 154(b) by 0 days.

(21) Appl. No.: 16/022,491

(22) Filed: Jun. 28, 2018

(51) Int. Cl.
  *B01D 67/00* (2006.01)
  *B01D 69/14* (2006.01)
  *B01D 71/76* (2006.01)
  *C07C 7/144* (2006.01)

(52) U.S. Cl.
  CPC ..... *B01D 67/0088* (2013.01); *B01D 67/0079* (2013.01); *B01D 69/142* (2013.01); *B01D 71/76* (2013.01); *C07C 7/144* (2013.01); *B01D 2257/702* (2013.01); *B01D 2311/04* (2013.01); *B01D 2311/10* (2013.01); *B01D 2311/14* (2013.01); *B01D 2325/10* (2013.01); *C10G 2400/20* (2013.01)

(58) Field of Classification Search
  CPC .......... B01D 67/0079; B01D 67/0088; B01D 71/76; B01D 69/142; B01D 2325/10; B01D 2257/702; B01D 2311/04; B01D 2311/10; B01D 2311/14; C07C 7/144; C10G 2400/20
  See application file for complete search history.

(56) References Cited

U.S. PATENT DOCUMENTS

| | | | | |
|---|---|---|---|---|
| 4,732,583 A | * | 3/1988 | Delong | B01D 53/22 62/624 |
| 5,157,201 A | * | 10/1992 | Norris | C07C 7/148 208/208 R |
| 5,252,219 A | * | 10/1993 | Xu | B01D 53/226 210/195.2 |
| 7,453,017 B2 | * | 11/2008 | Moon | B01J 23/58 502/262 |
| 2004/0215045 A1 | * | 10/2004 | Herrera | B01D 53/228 585/818 |
| 2017/0190640 A1 | * | 7/2017 | Noda | B01D 53/04 |

OTHER PUBLICATIONS

"Membrane Cascades" (http://www.separationprocesses.com/Membrane/MT_Chp04c.htnn, available on Apr. 15, 2012) (Year: 2012).*

* cited by examiner

*Primary Examiner* — Youngsul Jeong
*Assistant Examiner* — Jason Y Chong

(57) ABSTRACT

A process is provided to separate a hydrocarbon stream comprising a mixture of light olefins and light paraffins, the process comprising sending the hydrocarbon stream through a pretreatment unit to remove impurities selected from the group consisting of sulfur compounds, arsine, phosphine, methyl acetylene, propadiene, and acetylene to produce a treated hydrocarbon stream; vaporizing the treated hydrocarbon stream to produce a gaseous treated hydrocarbon stream; adding liquid or vapor water to the gaseous treated hydrocarbon stream; then contacting the gaseous treated hydrocarbon stream to a membrane in a membrane system comprising one or more membrane units to produce a permeate stream comprising about 96 to 99.9 wt % light olefins and a retentate stream comprising light paraffins.

16 Claims, 4 Drawing Sheets

MEMBRANE PROCESS FOR OLEFIN SEPARATION

FIELD OF THE INVENTION

This invention relates to a process for upgrading a low purity olefin/paraffin stream. More specifically, the invention relates to a process for upgrading a low olefin purity olefin/paraffin stream with less than about 80 wt % of olefin coming from an olefin/paraffin splitter with a mixture of olefins and a mixture of paraffins to higher olefin purity using a standalone membrane system without interaction with an existing column or any other column.

BACKGROUND OF THE INVENTION

Olefin producers usually sell or ship the low olefin purity olefin/paraffin stream at a lower value (refinery grade). Upgrading this stream on-site will bring much higher value due to higher purity, chemical grade or polymer grade olefin. The process disclosed in the current invention offers a process to upgrade low olefin purity olefin/paraffin stream at the customer site to a higher value stream, such as polymer grade propylene at high recovery. The process disclosed in the present invention also allows the installation of the membrane unit with a faster time (modular built) than a conventional distillation column, which takes longer to install, more costly and also takes up more footprint.

Separation of light olefins from paraffins is an energy intensive process. The current process involves traditional use of distillation columns which include 100-200 equilibrium trays which make these columns among the tallest in a refinery or petrochemical complex.

Over 170 Separex™ membrane systems have been installed in the world for gas separation applications such as for the removal of acid gases from natural gas, in enhanced oil recovery, and hydrogen purification. Two new Separex™ membranes (Flux+ and Select) have been commercialized recently by Honeywell UOP, Des Plaines, Ill. for carbon dioxide removal from natural gas. These Separex™ spiral wound membrane systems currently hold the membrane market leadership for natural gas upgrading. These membranes, however, do not have outstanding performance for olefin/paraffin separations. Development of new stable and very high selectivity membranes is critical for the future success of membranes for olefin/paraffin separation applications such as propylene/propane and ethylene/ethane separations.

Light olefins, such as propylene and ethylene, are produced as co-products from a variety of feedstocks in a number of different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by superfractionation with very high reflux ratios, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have the advantages of both low capital cost and high-energy efficiency compared to conventional separation methods for olefin/paraffin separations, such as propylene/propane and ethylene/ethane separations. Four main types of membranes have been reported for olefin/paraffin separations. These are facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability, due to carrier poisoning or loss, high cost, and low flux, currently limit practical applications of facilitated transport membranes.

Separation of olefins from paraffins via conventional polymer membranes has not been commercially successful due to inadequate selectivities and permeabilities of the polymer membrane materials, as well as due to plasticization and contamination issues. Polymers that are more permeable are generally less selective than are less permeable polymers. A general trade-off has existed between permeability and selectivity (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

More efforts have been undertaken to develop metal ion incorporated, high olefin/paraffin selectivity facilitated transport membranes. The high selectivity for olefin/paraffin separations is achieved by the incorporation of metal ions such as silver (I) or copper (I) cations into the solid nonporous polymer matrix layer on top of the highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes and the fixed site carrier facilitated transport membranes are less sensitive to the loss of metal cation carriers than the supported liquid facilitated transport membranes.

SUMMARY OF THE INVENTION

The invention involves a process to separate a hydrocarbon stream comprising a mixture of light olefins and light paraffins, particularly a process for upgrading an olefin/paraffin stream coming from an olefin/paraffin splitter with a mixture of olefins and a mixture of paraffins to higher olefin purity using a standalone membrane system without interaction with an existing column or any other column. The hydrocarbon stream that is sent to the standalone membrane system comprises a feed from a refinery grade propylene comprising less than about 80% of propylene. The impurities that need to be removed from the hydrocarbon stream before being treated by the membrane system of the present invention comprise arsine, phosphine, sulfur compounds, hydrogen, dienes and acetylenes. The first step of the process is to pretreat the hydrocarbon stream using a pretreatment unit which includes an adsorbent system followed by a selective hydrogenation unit to remove impurities to produce a treated hydrocarbon stream. The adsorbent system includes adsorbents such as those sold by UOP LLC to remove sulfur (COS, mercaptan, hydrogen sulfide), arsine, phosphine. While the adsorbents for sulfur and water removal are typically regenerable and installed in swing vessels, the adsorbents for arsine and phosphine are non-regenerable and installed in a guard bed. The selective hydrogenation unit include UOP commercial K-type of liquid process (KLP) or Pd type noble metal catalysts to selectively hydrogenate methyl acetylene and propadiene (MA/PD) to propylene since these compounds can permeate through the membrane with propylene product and also contaminate the membranes. The selective hydrogenation unit may include a second layer of a selective hydrogenation reduced metal platinum, palladium or nickel catalyst to actively consume extra hydrogen, which is another contaminant for the membrane in the reactor down to 0-10 ppm level, or preferably 0-5 ppm.

Then the treated hydrocarbon stream is vaporized to produce a gaseous treated hydrocarbon stream and add liquid or vapor water. The gaseous treated hydrocarbon stream is sent to a membrane system. The treated stream pressure at the membrane inlet is about 80-300 psig, preferably about 100-240 psig, and the membrane operation temperature is controlled at about 30-80° C., preferably about 45-65° C., with a humidity level at 40-100%, preferably 50-90%.

The membrane system described in the present invention can be a single stage membrane system comprising a single stage membrane unit, a two-stage membrane system comprising a first stage and a second stage membrane units, or a three or more-stage membrane system comprising a first stage, a second stage, a third stage or even more stage membrane units. To produce a single grade, high purity olefin such as polymer grade propylene (PGP, with about 99.5 wt % purity or higher), the second stage membrane permeate, the second and third stage membrane permeates, or the second, third and more stage membrane permeates can be recycled to the first stage feed. The same membrane is used for the single stage membrane system, the two-stage membrane system, or the three or more-stage membrane system. The olefin permeance of the membrane used for the membrane system in the present invention is about 33-245 GPU (1 GPU=$10^{-6}$ cm$^3$ (STP)/cm$^2$·sec·cmHg), preferably about 66-195 GPU and the olefin/paraffin selectivity of the membrane is in the range of about 80-1000, preferably in the range of about 100-800.

The standalone membrane system described in the present invention may comprise membrane units comprising membranes as recently described in US 2018/0001277 A1; US 2018/0001268 A1; and U.S. application Ser. No. 15/599,258 filed May 18, 2017 incorporated herein in their entireties.

The product stream from the permeate stream of the single stage membrane system may comprise 99.5 to 99.9% propylene. The hydrocarbon stream that is treated in the single stage membrane system may be a refinery grade propylene with about 70 wt % of propylene.

Sufficient water vapor is added to each hydrocarbon stream before each stream contacts a membrane unit so that the stream has from 40 to 100% humidity and more typically has from 50-90% humidity. Accordingly, water vapor is added to the feed streams for said single stage membrane unit in said single stage membrane system, said first stage membrane unit and second stage membrane unit in said two-stage membrane system, and said first stage membrane unit, second stage membrane unit, third stage and more stage membrane units in said three or more-stage membrane system before each of said feed streams enters the membrane unit. The membranes used in the first stage membrane unit, the second stage membrane unit, the third stage membrane unit, and the even more stage membrane unit are the same membranes that can be selected from the membranes as recently described in US 2017/0354918 A1; and U.S. application Ser. No. 15/615,134 filed Jun. 6, 2017. incorporated herein in their entireties.

The hydrocarbon stream is at a pressure from about 80 to about 300 psig, preferably from about 100 to about 240 psig, before entering a membrane unit and is at a temperature from about 30 to about 80° C., preferably from about 45 to about 65° C. The main light olefins that are produced by the present invention are ethylene and propylene. The process that is described herein includes details for the production of propylene, but a similar process may take place to produce ethylene.

Additional features and advantages of the invention will be apparent from the description of the invention, figures and claims provided herein.

DETAILED DESCRIPTION OF THE INVENTION

The invention relates to a process for upgrading a low olefin purity olefin/paraffin stream with less than about 80 wt % of olefin coming from an olefin/paraffin splitter with a mixture of olefins and a mixture of paraffins to higher olefin purity using a standalone membrane system without interaction with an existing column or any other column. The overall process includes a pretreatment system followed by membrane separation system. The pretreatment system includes adsorption units to remove impurities such as arsine, phosphine, sulfur compounds including mercaptans and other impurities present in the feed as well as a customized catalyst system that can selectively hydrogenate methylacetylene, acetylene, and propadiene contaminants to mono-olefins. While the adsorbents for sulfur removal are typically regenerable and installed in swing vessels, the adsorbents for arsine and phosphine are non-regenerable and installed in a guard bed. The selective hydrogenation unit include UOP commercial K-type of liquid process (KLP) or noble metal palladium catalyst to selectively hydrogenate methylacetylene, acetylene, and propadiene to ethylene and propylene since these compounds can permeate through the membrane with propylene product and also contaminate the membranes. The selective hydrogenation unit may include a second layer of a selective hydrogenation palladium catalyst such as reduced forms of Pt, Pd or Ni, for example, if the K-type catalyst is used in the first layer to actively consume extra $H_2$, which is another contaminant for the membrane in the reactor down to 0-10 ppm level, or preferably 0-5 ppm.

The treated liquid hydrocarbon feed is then vaporized and heated to about 30-80° C., preferably 45-65° C. and added with water to 40-100% humidity, preferably 50-90% humidity before entering the membrane system. The treated hydrocarbon stream pressure at the membrane inlet is about 80 to about 300 psig, preferably about 100 to about 240 psig.

Figure 1:
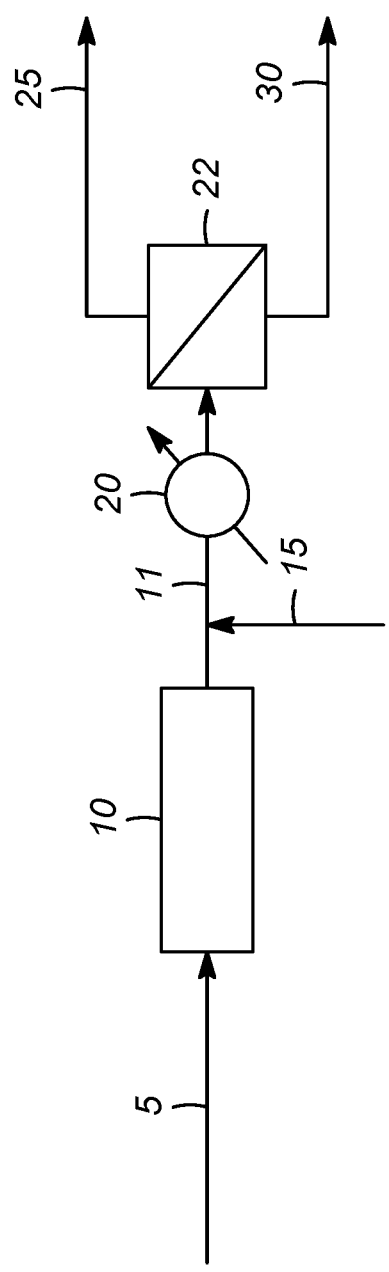
FIG. 1 is a single stage membrane system to produce a polymer grade propylene stream.

In one embodiment as shown in FIG. 1, a typical treated hydrocarbon feed such as a low purity refinery grade propylene comprising about 70 wt % propylene enters a single stage membrane system to produce a high purity propylene permeate product with 99.5 wt % of propylene and approximately 70% propylene recovery (propylene recovery is defined as the amount of propylene in the permeate divided by the amount of propylene in the feed). The concentration of propylene in the retentate from the single stage membrane system is in the range of 40-45 wt %. The propylene permeance of the membrane used for the single stage membrane system in the present invention is about 33-245 GPU, preferably about 66-195 GPU and the propylene/propane selectivity is in the range of about 80-1000, preferably in the range of about 100-800.

In FIG. 1, a feed 5 as described above is sent to a pretreatment zone 10 to provide a treated stream 11 that is heated by heater 20 and enters membrane unit 22 to be separated into a permeate 25 and a residue 30. Water vapor is added at 15.

Figure 2:
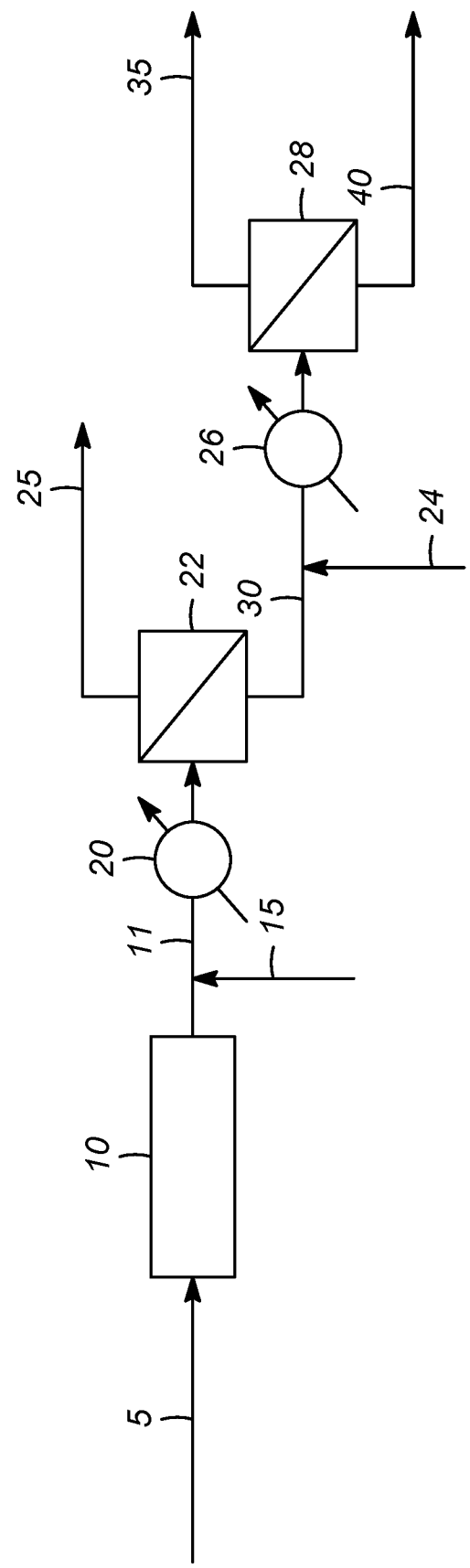
FIG. 2 is a two-stage membrane system to upgrade propylene stream.

In a second embodiment of the invention as shown in FIG. 2, a typical treated hydrocarbon feed such as a low purity refinery grade propylene comprising about 70 wt % propylene is vaporized and heated to about 30-80° C., preferably 45-65° C. and added with water to 40-100% humidity, preferably 50-90% humidity before entering a two-stage membrane system. The treated hydrocarbon stream pressure at the membrane inlets for both the first stage membrane unit and the second stage membrane unit is about 80 to about 300 psig, preferably about 100 to about 240 psig. The treated hydrocarbon stream enters a two-stage membrane system to produce high purity propylene permeate products with about 98 wt % to 99.5 wt % of propylene and improved propylene recovery to about 92.5% compared to the single stage membrane system as shown in FIG. 1. In the two-stage membrane system, about 69% of propylene recovery goes to the premium propylene product at 99.5 wt % purity in the permeate stream of the first stage membrane and an additional about 23.5% propylene recovery goes to a propylene product at about 98.4 wt % purity in the permeate stream of the second stage membrane. The concentration of propylene in the retentate of the first stage membrane is in the range of about 40-45 wt % and the concentration of propylene in the retentate of the second stage membrane is about 35 wt %. The retentate of the first stage membrane is humidified to 40-100% humidity, preferably 50-90% humidity and heated to about 30-80° C., preferably 45-65° C. before entering to the second stage membrane unit. The membrane used in the first stage membrane unit and that used in the second stage membrane unit in the two-stage membrane system described in the present invention are the same membrane with propylene permeance of about 33-245 GPU, preferably about 66-195 GPU and high propylene/propane selectivity in the range of about 80-1000, preferably in the range of about 100-800.

In FIG. 2, a feed 5 as described above is sent to a pretreatment zone 10 to provide a treated stream 11 that is heated by heater 20 and enters membrane unit 22 to be separated into a permeate stream 25 and a retentate 30. Water vapor is added at 15 and 24. Retentate 30 is heated by heater 26 and passes through a second membrane unit 28 to be separated into second permeate stream 35 and second retentate 40.

Figure 3:
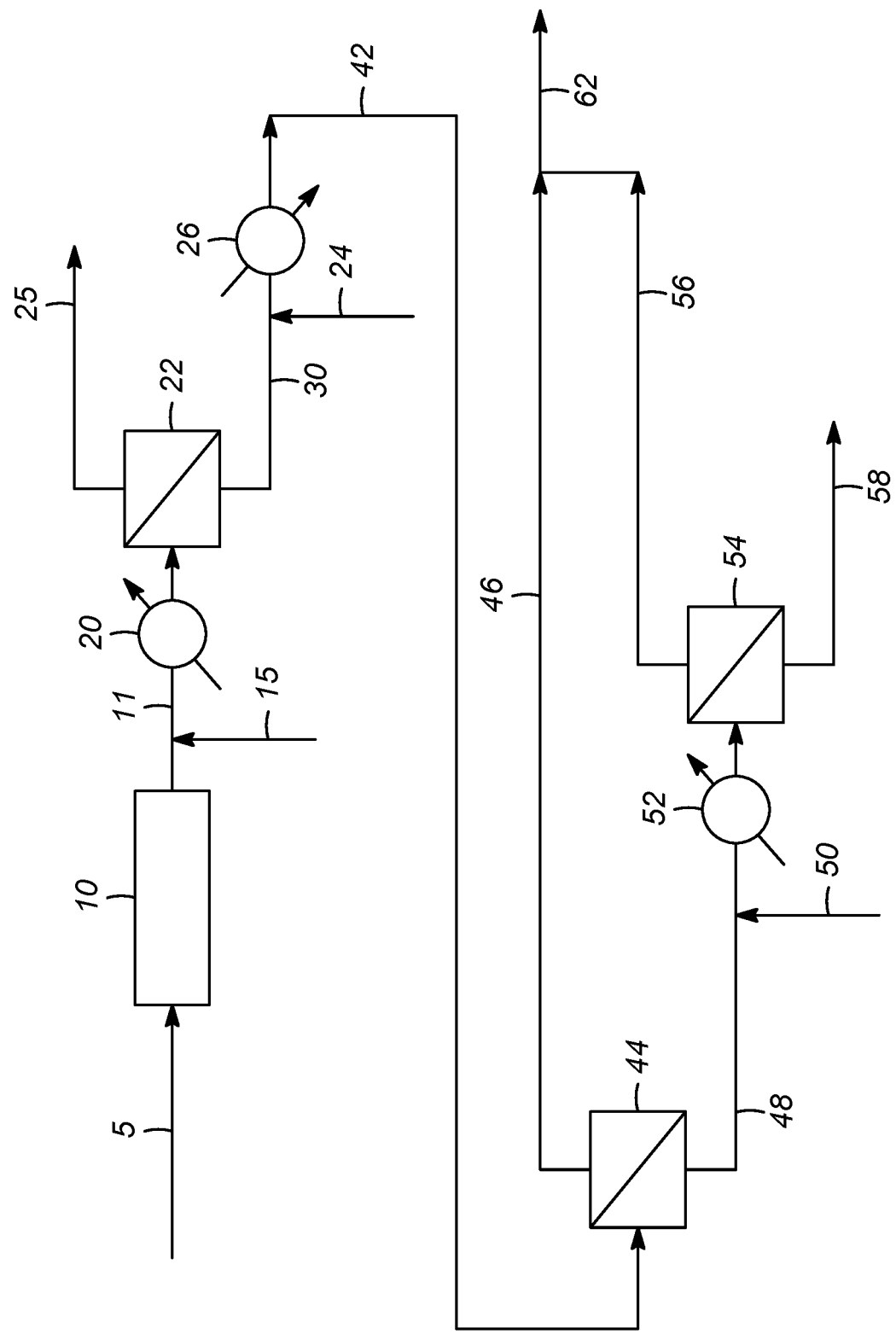
FIG. 3 is a three-stage membrane system to upgrade propylene stream.

In a third embodiment of the invention as shown in FIG. 3, a typical treated hydrocarbon feed such as a low purity refinery grade propylene comprising about 70 wt % propylene is vaporized and heated to about 30-80° C., preferably 45-65° C. and added with water to 40-100% humidity, preferably 50-90% humidity before entering a three-stage membrane system. The treated hydrocarbon stream pressure at the membrane inlets for the first stage membrane unit, the second stage membrane unit, and the third stage membrane unit is about 80 to about 300 psig, preferably about 100 to about 240 psig. The treated hydrocarbon stream enters a three-stage membrane system to produce high purity propylene permeate products with about 96 wt % to 99.5 wt % of propylene and improved overall propylene recovery to about 96.4% compared to the single stage membrane system as shown in FIG. 1 and the two-stage membrane system as shown in FIG. 2. In the three-stage membrane system, about 69% of propylene recovery goes to the premium propylene product at 99.5 wt % purity in the permeate stream of the first stage membrane, about 23.5% of propylene recovery goes to a propylene product at about 98.4 wt % purity in the permeate stream of the second stage membrane, and about 3.9% of propylene recovery goes to a propylene product at about 90.7 wt % purity in the permeate stream of the third stage membrane. The secondary and tertiary propylene product can be combined to produce a 96.9 wt % purity propylene product. In some cases, additional stages can be added to the multi-stage membrane system process to further improve the propylene recovery. The concentration of propylene in the retentate of the first stage membrane is in the range of about 40-45 wt %, the concentration of propylene in the retentate of the second stage membrane is about 35 wt % and the concentration of propylene in the retentate of the third stage membrane is about 8.6 wt %. The retentates of the first stage membrane unit and the second stage membrane unit are humidified to 40-100% humidity, preferably 50-90% humidity and heated to about 30-80° C., preferably 45-65° C. before entering to the second stage membrane unit and the third stage membrane unit, respectively. The membrane used in the first stage membrane unit, that used in the second stage membrane unit, and that used in the third stage membrane unit in the three-stage membrane system described in the present invention are the same membrane with propylene permeance of about 33-245 GPU, preferably about 66-195 GPU and high propylene/propane selectivity in the range of about 80-1000, preferably in the range of about 100-800.

In FIG. 3, a feed 5 as described above is sent to a pretreatment zone 10 to provide a treated stream 11 that is heated by heater 20 and enters membrane unit 22 to be separated into a permeate stream 25 and a retentate 30. Water vapor is added at 15, 24 and 50. Retentate 30 is heated by heater 26 to produce a heated retentate 42 that passes through a second membrane unit 44 to be separated into second permeate stream 46 and second retentate 48. Second permeate stream is mixed with a third permeate stream 56 to become combined permeate stream 62. Retentate 48 is sent through heater 52 to pass through a third membrane unit 54 to be separated into permeate stream 56 and third retentate 58.

Figure 4:
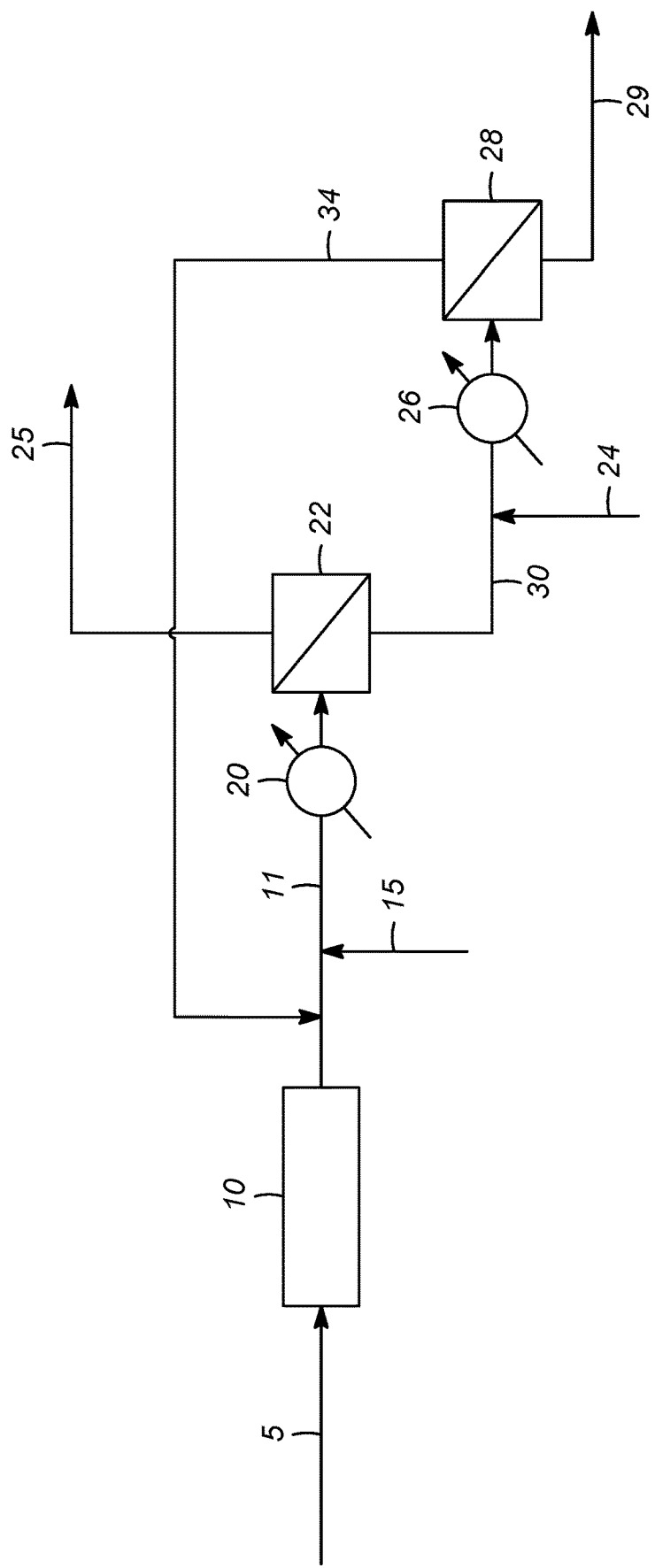
FIG. 4 is a two-stage membrane system to produce a single polymer grade propylene stream.

In a fourth embodiment of the invention as shown in FIG. 4, a typical treated hydrocarbon feed such as a low purity refinery grade propylene comprising about 70 wt % propylene is vaporized and heated to about 30-80° C., preferably 45-65° C. and added with water to 40-100% humidity, preferably 50-90% humidity before entering a two-stage membrane system from which the permeate of the second stage membrane unit is recycled to the membrane inlet of the first stage membrane unit to provide a single polymer grade propylene (PGP with propylene purity of 99.5 wt % or higher) product. The treated hydrocarbon stream pressure at the membrane inlets for both the first stage membrane unit and the second stage membrane unit is about 80 to about 300 psig, preferably about 100 to about 240 psig. The treated hydrocarbon stream enters a two-stage membrane system to produce a high purity single PGP product with propylene purity of 99.5 wt % or higher in the permeate of the first stage membrane unit and the permeate of the second stage membrane is recycled back to the membrane inlet of the first stage membrane unit. For example, the second stage permeate with about 98 wt % propylene purity is recompressed, cooled and controlled at about 30-80° C., preferably at about 45-65° C., and combined with the treated hydrocarbon feed to the first stage membrane unit. The permeate of the first stage membrane unit provides the high purity product with about 99.7 wt % propylene and the total propylene recovery is about 91.6%. In the two-stage membrane system with the permeate of the second stage membrane unit recycled back to the feed of the first stage membrane unit, the concentration of propylene in the retentate of the first stage membrane is in the range of about 40-45 wt % and the concentration of propylene in the retentate of the second stage membrane is about 16 wt %. The retentate of the first stage membrane is humidified to 40-100% humidity, preferably 50-90% humidity and heated to about 30-80° C., preferably 45-65° C. before entering to the second stage membrane unit. The membrane used in the first stage membrane unit and that used in the second stage membrane unit in the two-stage membrane system descried in the present invention are the same membranes with propylene permeance of about 33-245 GPU, preferably about 66-195 GPU and high propylene/propane selectivity in the range of about 80-1000, preferably in the range of about 100-800.

The two-stage membrane system with the permeate of the second stage membrane unit recycled back to the feed of the first stage membrane unit as shown in FIG. 4 is capable of producing 98 KMTA (thousands of metric tons per annum) polymer grade propylene product with at least 99.5 wt % propylene. All concentrations that are discussed are regarding wt % propylene. The hydrocarbon feed steam for the first stage membrane unit as shown in FIG. 4 has about 70 wt % of propylene with a total volume of hydrocarbon processed of 154 KMTA and the volume of the by-product in the retentate of the second stage membrane unit is about 56 KMTA. In FIG. 4, a feed 5 as described above is sent to a pretreatment zone 10 to provide a treated stream 11 that is heated by heater 20 and enters membrane unit 22 to be separated into a permeate stream 25 and a retentate 30. Water vapor is added at 15 and 24. Retentate 30 is heated by heater 26 and passes through a second membrane unit 28 to be separated into second permeate stream 34 and second retentate 29. Second permeate stream is recycled to be combined with stream 11 to pass through the membrane units again.

Figure 5:
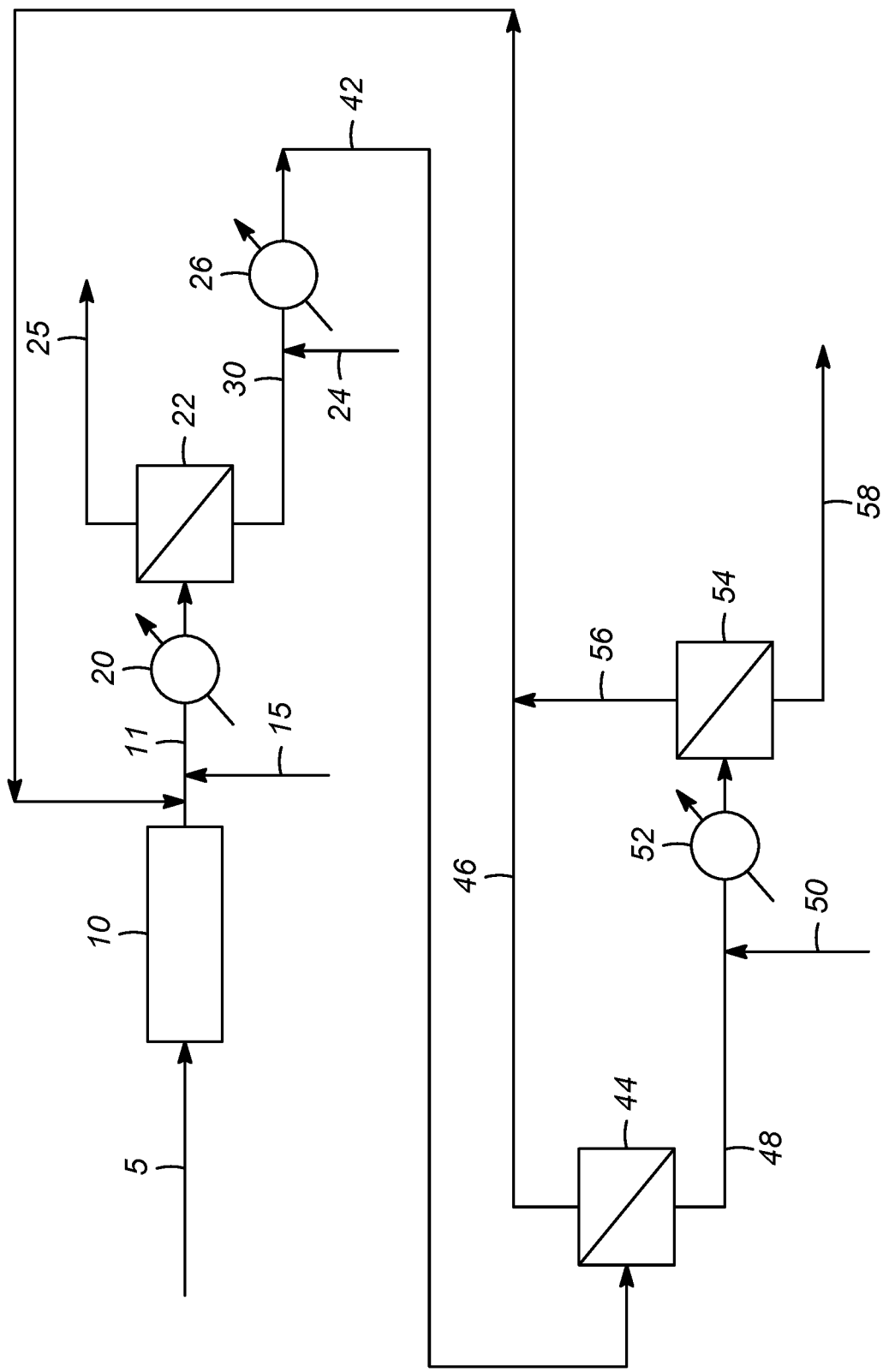
FIG. 5 is a three-stage membrane system to produce a single polymer grade propylene stream.

In a fifth embodiment of the invention as shown in FIG. 5, a typical treated hydrocarbon feed such as a low purity refinery grade propylene comprising about 70 wt % propylene is vaporized and heated to about 30-80° C., preferably 45-65° C. and added with water to 40-100% humidity, preferably 50-90% humidity before entering a three-stage membrane system from which the permeate of the third stage membrane unit is combined with the permeate of the second stage membrane unit, recompressed together, and recycled to the feed of the first stage membrane unit to provide a single polymer grade propylene (PGP with propylene purity of about 99.5 wt % or 99.7 wt % or higher) product from the permeate of the first stage membrane unit. The treated hydrocarbon stream pressure at the membrane inlets for the first stage membrane unit, the second stage membrane unit, and the third stage membrane unit is about 80 to about 300 psig, preferably about 100 to about 240 psig. The treated hydrocarbon stream enters a three-stage membrane system to produce a high purity single PGP product with propylene purity of about 99.5 wt % or 99.7 wt % in the permeate of the first stage membrane unit and the permeate of the third stage membrane unit is combined with the permeate of the second stage membrane unit, recompressed together, cooled, controlled at about 30-80° C., preferably at about 45-65° C., and combined with the treated hydrocarbon feed to the first stage membrane unit to provide a single polymer grade propylene (PGP with propylene purity of about 99.7 wt % or higher) product from the permeate of the first stage membrane unit. The total propylene recovery is about 95.6%.

In FIG. 5, a feed 5 as described above is sent to a pretreatment zone 10 to provide a treated stream 11 that is heated by heater 20 and enters membrane unit 22 to be separated into a permeate stream 25 and a retentate 30. Water vapor is added at 15, 24 and 50. Retentate 30 is heated by heater 26 to produce a heated retentate 42 that passes through a second membrane unit 44 to be separated into second permeate stream 46 and second retentate 48. Second permeate stream is mixed with a third permeate stream 56 from third membrane unit 54. Retentate 48 is sent through heater 52 to pass through third membrane unit 54 to be separated into third permeate stream 56 and third retentate 58. Third permeate stream 56 is combined with second permeate stream 46 to be recycled to treated stream 11 to be sent through the membrane units again.

In the three-stage membrane system with the permeate of the third stage membrane unit and the permeate of the second stage membrane unit combined and recycled back to the feed of the first stage membrane unit, the concentration of propylene in the retentate of the third stage membrane is about 9.1 wt %. The retentate of the first stage membrane and the retentate of the second stage membrane unit are humidified to 40-100% humidity, preferably 50-90% humidity and heated to about 30-80° C., preferably 45-65° C. before entering to the second stage membrane unit and the third stage membrane unit, respectively. The membrane used in the first stage membrane unit, that used in the second stage membrane unit, and that used in the third stage membrane unit in the three-stage membrane system as shown in FIG. 5 in the present invention are the same membranes with propylene permeance of about 33-245 GPU, preferably about 66-195 GPU and high propylene/propane selectivity in the range of about 80-1000, preferably in the range of about 100-800. In some cases, additional stages of membrane units are used and recombining permeates of the additional stages with the permeates of the third and second stage membrane units, recompressing the combined permeates, and recycling the combined permeates to the feed of the first stage membrane unit results in further improved overall propylene recovery. For example, with the addition of a fourth stage membrane unit, the recovery of propylene improves to 96.4% and propane rich product in the retentate of the fourth stage membrane unit contains about 7.6 wt % of propylene.

The propane rich product, with 7-10% wt propylene, can be compressed, cooled and further contacted with a finishing reactor, or a hydrogenation reactor (UOP complete saturation process—CSP), to reduce the concentration of propylene to less than or equal to 5% by volume and as low as 100 wt-ppm. The finishing reactor uses a commercial CSP catalyst with controlled hydrogen addition and residence time in the reactor to achieve targeted activity and selectivity.

The three-stage membrane system with the permeate of the third stage membrane unit and the permeate of the second stage membrane unit combined and recycled back to the feed of the first stage membrane unit as shown in FIG. 5 is capable of producing 102 KMTA polymer grade propylene product with at least 99.5 wt % or 99.7 wt % propylene. The hydrocarbon feed steam for the first stage membrane unit as shown in FIG. 5 has about 70 wt % of propylene with a total volume of hydrocarbon processed of 154 KMTA and the volume of the by-product in the retentate of the third stage membrane unit is about 52 KMTA.

The membranes used in the single stage membrane system, the two-stage membrane systems without or with the recycle of the permeate of the second stage membrane unit to the feed of the first stage membrane unit, and the three-stage membrane systems without or with the recycle of the permeates of the second stage membrane unit and the third stage membrane unit to the feed of the first stage membrane unit may be the membranes described in US 2018/0001277 A1; US 2018/0001268 A1; and U.S. application Ser. No. 15/599,258 filed May 18, 2017 incorporated herein in their entireties.

Some of the facilitated transport membranes described in US 2018/0001277 A1 can be used in the membrane systems in the present invention, wherein said facilitated transport membrane may comprise a carboxylic acid functional group containing polyimide wherein the carboxylic acid functional groups are ion-exchanged or chelated with metal cations such as silver (I) or copper (I) cations. The metal cation ion-exchanged or chelated carboxylic acid functional group containing polyimide described in US 2018/0001277 A1 comprising a plurality of repeating units of formula (I)

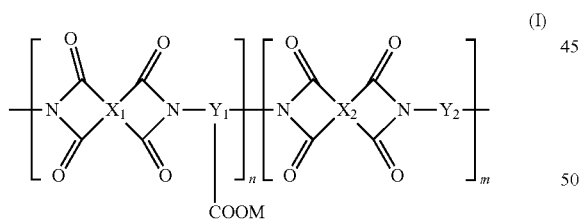

wherein X1 and X2 are selected from the group consisting of

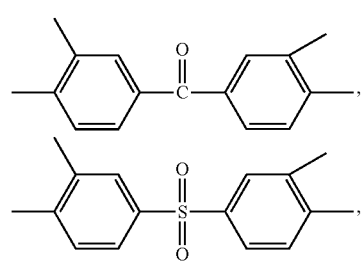

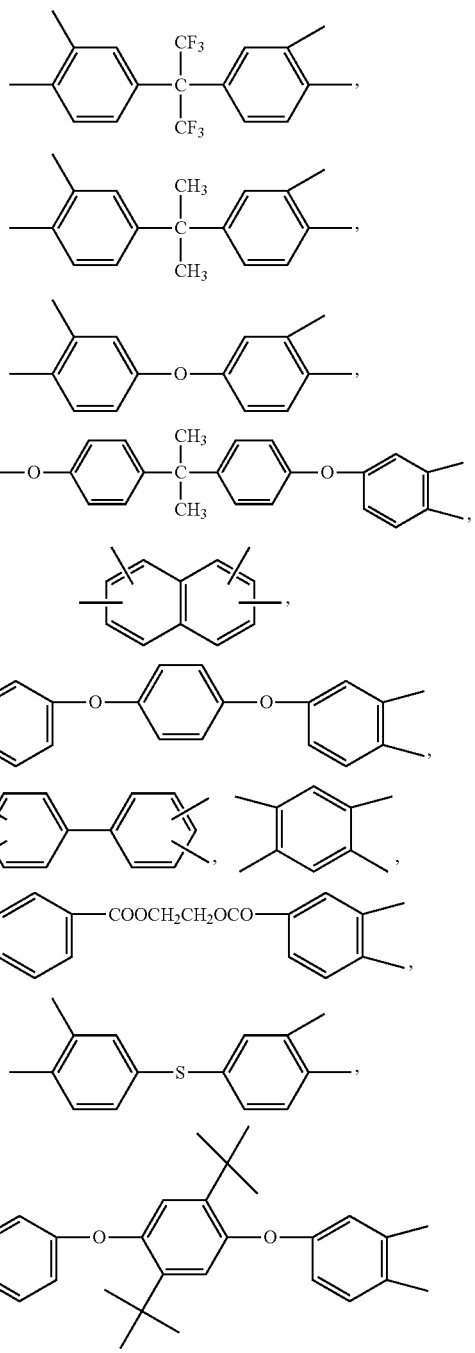

and mixtures thereof, and wherein X1 and X2 may be the same or different from each other; wherein $Y_1$—COOM is selected from the group consisting of

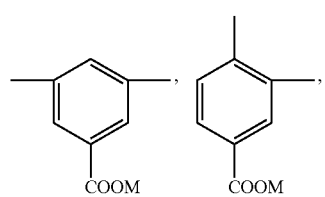

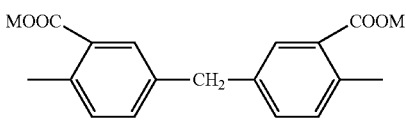

and mixtures thereof and wherein M is selected from silver (I) cation or copper (I) cation; wherein Y2 is selected from the group consisting of

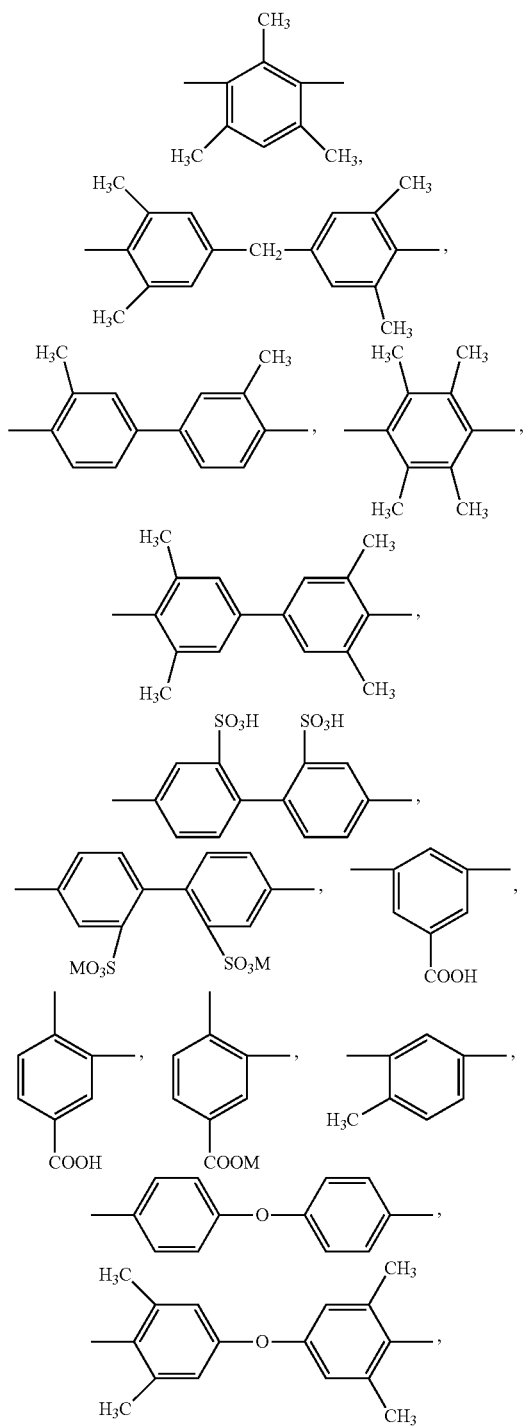

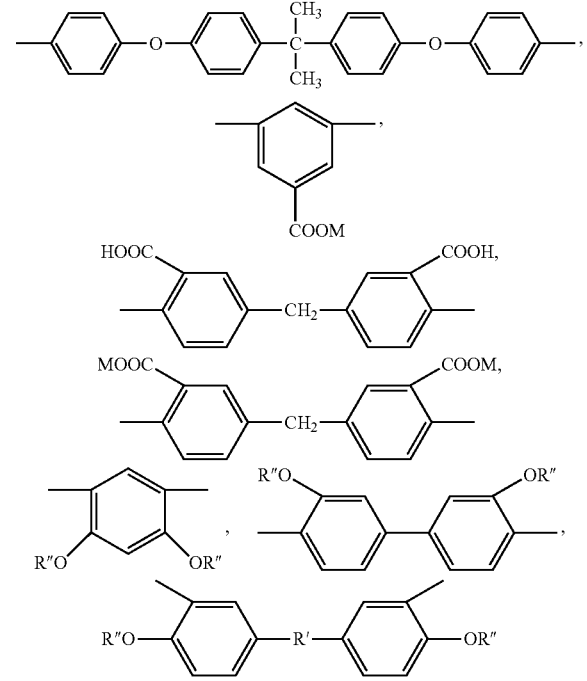

and mixtures thereof, and —R'— is selected from the group consisting of

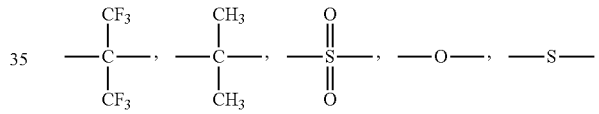

and mixtures thereof, and —R"— is selected from the group consisting of —H, COCH$_3$, and mixtures thereof, and M is selected from silver (I) cation or copper (I) cation; wherein n and m are independent integers from 2 to 500; and wherein n/m is in a range of 1:0 to 1:10, and preferably n/m is in a range of 1:0 to 1:5.

Preferably, X1 and X2 are selected from the group consisting of

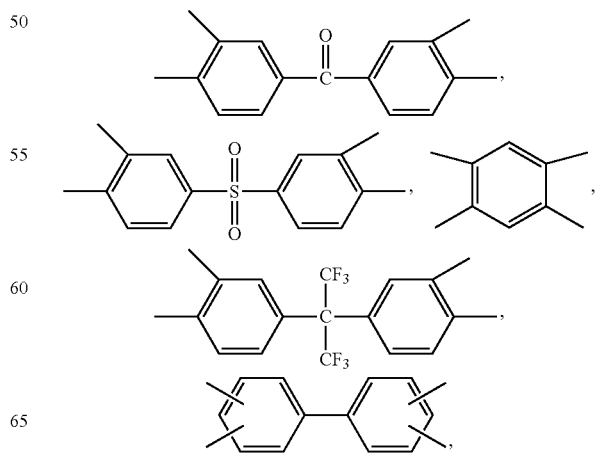

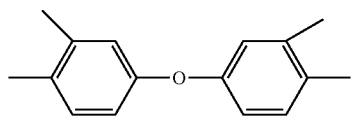

and mixtures thereof, and wherein X1 and X2 may be the same or different from each other; preferably Y1-COOM is selected from the group consisting of

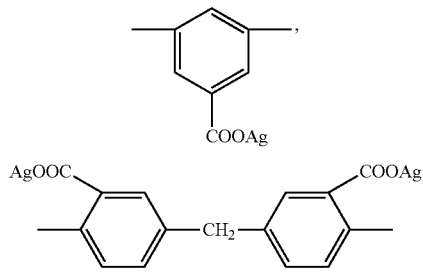

and mixtures thereof; preferably Y2 is selected from the group consisting of

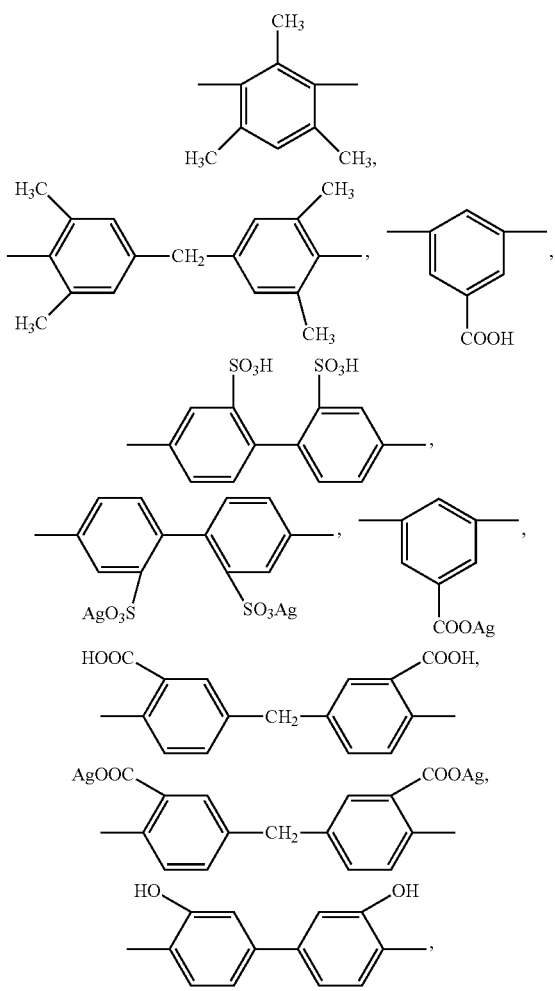

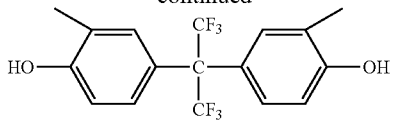

and mixtures thereof.

The stable high performance facilitated transport membrane described in US 2018/0001277 A1 comprising an asymmetric integrally-skinned polymeric membrane wherein the pores on a relatively porous, thin, dense skin layer of the membrane comprises a hydrophilic polymer, a metal salt or a mixture of a metal salt and hydrogen peroxide, wherein said asymmetric integrally-skinned polymeric membrane comprises a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure can be used as the membranes in the single stage membrane system, the two-stage membrane systems without or with the recycle of the permeate of the second stage membrane unit to the feed of the first stage membrane unit, and the three-stage membrane systems without or with the recycle of the permeates of the second stage membrane unit and the third stage membrane unit to the feed of the first stage membrane unit in the present invention. The stable high performance facilitated transport membrane described in US 2018/0001277 A1 used as the membranes in the membrane systems in the present invention comprises a polymer selected from a group consisting of a polyimide, a blend of two or more different polyimides, and a blend of a polyimide and a polyethersulfone and wherein the polyimide can be selected from the group consisting of poly(2,2'-bis-(3,4-dicarboxyphenyl)hexafluoropropane dianhydride-3,3',5,5'-tetramethyl-4,4'-methylene dianiline) polyimide derived from a polycondensation reaction of 2,2'-bis-(3,4-dicarboxyphenyl)hexafluoropropane dianhydride (6FDA) with 3,3',5,5'-tetramethyl-4,4'-methylene dianiline (TMMDA), poly(3,3',4,4'-diphenylsulfone tetracarboxylic dianhydride-3,3',5,5'-tetramethyl-4,4'-methylene dianiline) polyimide derived from the polycondensation reaction of 3,3',4,4'-diphenylsulfone tetracarboxylic dianhydride (DSDA) with TMMDA, poly(3,3',4,4'-benzophenone tetracarboxylic dianhydride-pyromellitic dianhydride-3,3',5,5'-tetramethyl-4,4'-methylene dianiline) polyimide derived from the polycondensation reaction of a mixture of 3,3',4,4'-benzophenone tetracarboxylic dianhydride (BTDA) and pyromellitic dianhydride (PMDA) with TMMDA, poly(3,3',4,4'-benzophenone tetracarboxylic dianhydride-pyromellitic dianhydride-2,4,6-trimethyl-1,3-phenylenediamine) polyimide derived from the polycondensation reaction of a mixture of BTDA and PMDA with 2,4,6-trimethyl-1,3-phenylenediamine (TMPDA), poly(3,3',4,4'-benzophenone tetracarboxylic dianhydride-pyromellitic dianhydride-2,4,6-trimethyl-1,3-phenylenediamine-2,4-toluenediamine) polyimide derived from the polycondensation reaction of a mixture of BTDA and PMDA with a mixture of TMPDA and 2,4-toluenediamine (2,4-TDA), and poly(3,3',4,4'-diphenylsulfone tetracarboxylic dianhydride-3,3',5,5'-tetramethyl-4,4'-methylene dianiline-4,4'-diamino-2-methylazobenzene) polyimide derived from the polycondensation reaction of DSDA with a mixture of TMMDA and 4,4'-diamino-2-methylazobenzene (DAMAB).

The membranes used in all of the membrane systems in the present invention may comprise a co-cast thin film composite flat sheet membrane comprising an asymmetric porous non-selective support layer and an asymmetric integrally skinned polyimide-containing selective layer on top of said asymmetric porous non-selective support layer wherein said asymmetric porous non-selective support layer comprises a non-polyimide polymer or a mixture of a non-polyimide polymer and a polyimide polymer and wherein the weight ratio of said non-polyimide polymer to said polyimide polymer in said mixture is in a range of 20:1 to 2:1 as described in U.S. application Ser. No. 15/599,258.

The membranes used in the membrane systems in the present invention may be the membranes as recently described in US 2017/0354918 A1; U.S. application Ser. No. 15/615,134 filed Jun. 6, 2017; and U.S. Provisional Application No. 62/549,820 filed Aug. 24, 2017 incorporated herein in their entireties.

The high selectivity facilitated transport membrane disclosed in US 2017/0354918 A1 comprising a relatively hydrophilic, very small pore, nanoporous support membrane, a hydrophilic polymer inside the very small nanopores on the skin layer surface of the support membrane, a thin, nonporous, hydrophilic polymer layer coated on the surface of the support membrane, and metal salts incorporated in the hydrophilic polymer layer coated on the surface of the support membrane and the hydrophilic polymer inside the very small nanopores can be used as the membranes in the membrane systems described in the present invention. The relatively hydrophilic, very small pore, nanoporous support membrane used for the preparation of the new facilitated transport membrane comprising a relatively hydrophilic, very small pore, nanoporous support membrane, a hydrophilic polymer inside the very small nanopores on the surface of the support membrane, a thin, nonporous, hydrophilic polymer layer coated on the surface of said support membrane, and metal salts incorporated in the hydrophilic polymer layer coated on the surface of the support membrane and said hydrophilic polymer inside the very small nanopores disclosed in the present invention comprises a relatively hydrophilic polymer selected from a group consisting of, but is not limited to, polyethersulfone (PES), a blend of PES and polyimide, cellulose acetate, cellulose triacetate, and a blend of cellulose acetate and cellulose triacetate. The relatively hydrophilic, very small pore, nanoporous support membrane described in the current invention has an average pore diameter of less than 10 nm on the membrane skin layer surface. The relatively hydrophilic, very small pore, nanoporous support membrane described in the current invention can be either asymmetric integrally skinned membrane or thin film composite (TFC) membrane with either flat sheet (spiral wound) or hollow fiber geometry.

The hydrophilic polymer inside the very small nanopores on the surface of the relatively hydrophilic, very small pore, nanoporous support membrane of the facilitated transport membrane described in US 2017/0354918 A1 can be selected from, but is not limited to, a group of hydrophilic polymers containing chitosan, sodium carboxylmethyl-chitosan, carboxylmethyl-chitosan, hyaluronic acid, sodium hyaluronate, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The metal salts incorporated in the hydrophilic polymer layer coated on the surface of said support membrane and the hydrophilic polymer inside the very small nanopores of the facilitated transport membrane described in US 2017/ 0354918 A1 are preferred to be selected from silver salts or copper salts, such as silver(I) nitrate or copper(I) chloride.

The dried, relatively hydrophilic, very small pore, nanoporous support membrane comprising hydrophilic polymers inside the very small nanopores on the membrane surface described in US 2017/0354918 A1 has carbon dioxide permeance of 800-10,000 GPU and no carbon dioxide/methane selectivity at 50° C. under 30-100 psig 10% $CO_2$/90% $CH_4$ mixed gas feed pressure.

The new facilitated transport membrane disclosed in U.S. application Ser. No. 15/615,134 comprising a nanoporous polyethersulfone/polyvinylpyrrolidone blend support membrane, a hydrophilic polymer inside nanopores of said support membrane, a hydrophilic polymer coating layer on a surface of the support membrane and metal salts in the hydrophilic polymer coating layer and in the hydrophilic polymer inside the nanopores of said support membrane can also be used as the membranes in the membrane systems described in the present invention.

A membrane comprising a polyethersulfone/polyethylene oxide-polysilsesquioxane blend support membrane comprising a polyethylene oxide-polysilsesquioxane polymer and a polyethersulfone polymer; a hydrophilic polymer inside the pores on the skin layer surface of the polyethersulfone/polyethylene oxide-polysilsesquioxane blend support membrane; a hydrophilic polymer coated on the skin layer surface of the polyethersulfone/polyethylene oxide-polysilsesquioxane blend support membrane, and metal salts incorporated in the hydrophilic polymer coating layer and the skin layer surface pores of the polyethersulfone/polyethylene oxide-polysilsesquioxane blend support membrane can also be used as the membranes in the membrane systems described in the present invention.

Any of the above membrane units, conduits, unit devices, scaffolding, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process to separate a hydrocarbon stream comprising a mixture of light olefins and light paraffins, the process comprising sending the hydrocarbon stream through a pretreatment unit to remove impurities selected from the group consisting of sulfur compounds, arsine, phosphine, acetylene, methylacetylene, and propadiene to produce a treated hydrocarbon stream; vaporizing the treated hydrocarbon stream to produce a gaseous treated hydrocarbon stream; adding liquid or vapor water to the gaseous treated hydrocarbon stream; then contacting the gaseous treated hydrocarbon stream to a membrane in a membrane system comprising one or more membrane units to produce a permeate stream comprising about 96 to 99.9 wt % light olefins and a retentate stream comprising light paraffins. An embodiment of the invention is one, any or all of prior embodiments in this paragraph up through the first embodiment in this paragraph wherein the water is added to the hydrocarbon stream before vaporizing it. An embodiment of the invention is one, any or all of prior embodiments in this paragraph up through the first embodiment in this paragraph wherein the treated hydrocarbon stream is sent through a selective hydrogenation unit to selectively hydrogenate methyl acetylene, acetylene, and propadiene. An embodiment of the invention is one, any or all of prior embodiments in this paragraph up through the first embodiment in this paragraph wherein the selective hydrogenation unit removes hydrogen to reduce the level of hydrogen in the treated hydrocarbon stream to about 5 ppm or less. An embodiment of the invention is one, any or all of prior embodiments in this paragraph up through the first embodiment in this paragraph wherein the selective hydrogenation unit contains a catalyst selected from the group consisting of reduced forms of Pt, Pd and Ni catalysts. An embodiment of the invention is one, any or all of prior embodiments in this paragraph up through the first embodiment in this paragraph wherein the hydrocarbon stream comprises less than about 80 wt % light olefins. An embodiment of the invention is one, any or all of prior embodiments in this paragraph up through the first embodiment in this paragraph wherein the hydrocarbon stream comprises less than about 70 wt % light olefins. An embodiment of the invention is one, any or all of prior embodiments in this paragraph up through the first embodiment in this paragraph wherein the light olefins comprise ethylene or propylene. An embodiment of the invention is one, any or all of prior embodiments in this paragraph up through the first embodiment in this paragraph wherein sufficient liquid or water vapor is added to the gaseous treated hydrocarbon so that the gaseous treated hydrocarbon stream has from 50 to 90% humidity when contacting the membrane. An embodiment of the invention is one, any or all of prior embodiments in this paragraph up through the first embodiment in this paragraph wherein the membrane system comprises a single stage membrane. An embodiment of the invention is one, any or all of prior embodiments in this paragraph up through the first embodiment in this paragraph wherein the membrane system comprises a two stage membrane system wherein a retentate from a first membrane unit is contacted to a second membrane unit to produce a second permeate stream and a second retentate stream. An embodiment of the invention is one, any or all of prior embodiments in this paragraph up through the first embodiment in this paragraph wherein the second permeate stream is recycled to the gaseous treated hydrocarbon stream. An embodiment of the invention is one, any or all of prior embodiments in this paragraph up through the first embodiment in this paragraph wherein the membrane system comprises a three stage membrane system wherein a retentate from a first membrane unit is contacted to a second membrane unit to produce a second permeate stream and a second retentate stream and the second retentate stream is sent to a third membrane unit to produce a third permeate stream and a third retentate. An embodiment of the invention is one, any or all of prior embodiments in this paragraph up through the first embodiment in this paragraph wherein the third permeate is combined with said second permeate and recycled to the gaseous treated hydrocarbon stream. An embodiment of the invention is one, any or all of prior embodiments in this paragraph up through the first embodiment in this paragraph wherein the membrane system is operated at a temperature from about 30 to 80° C. An embodiment of the invention is one, any or all of prior embodiments in this paragraph up through the first embodiment in this paragraph wherein the hydrocarbon stream is at a pressure from about 80 to about 300 psig before entering a membrane unit. An embodiment of the invention is one, any or all of prior embodiments in this paragraph up through the first embodiment in this paragraph wherein the concentration of propylene in the retentate from a single stage membrane system in about 40-45 wt %. An embodiment of the invention is one, any or all of prior embodiments in this paragraph up through the first embodiment in this paragraph wherein a membrane used in the membrane system has a propylene permeance of about 33-245 GPU and a propylene/propane selectivity in a range of about 80-1000. An embodiment of the invention is one, any or all of prior embodiments in this paragraph up through the first embodiment in this paragraph wherein the permeate stream comprises about 99 to 99.5 wt % propylene. An embodiment of the invention is one, any or all of prior embodiments in this paragraph up through the first embodiment in this paragraph wherein the retentate comprises about 7 to 10 wt % propylene. An embodiment of the invention is one, any or all of prior embodiments in this paragraph up through the first embodiment in this paragraph wherein the process further comprises at least one of: sensing at least one parameter of the process and generating a signal from the sensing; sensing at least one parameter of the process and generating data from the sensing; generating and transmitting a signal; and generating and transmitting data.

The invention claimed is:

1. A process to separate a hydrocarbon stream comprising a mixture of light olefins and light paraffins, said process comprising:
   sending said hydrocarbon stream through a pretreatment unit to remove impurities selected from the group consisting of sulfur compounds, arsine, and phosphine, and then through a selective hydrogenation unit to selectively hydrogenate methyl acetylene and acetylene to produce a treated liquid hydrocarbon stream;
   adding liquid or vapor water to said treated liquid hydrocarbon stream;
   vaporizing said treated liquid hydrocarbon stream to produce a gaseous treated hydrocarbon stream; and then contacting said gaseous treated hydrocarbon stream to a membrane unit in a membrane system comprising one or more of the membrane units to produce a permeate stream comprising about 96 to 99.9 wt % light olefins and a retentate stream comprising light paraffins, wherein the membrane unit comprises a facilitated transport membrane having a light olefin permeance of about 33-245 GPU and a light olefin/light paraffin selectivity in a range of about 80 to 1000.

2. The process of claim 1 wherein said selective hydrogenation unit removes hydrogen to reduce a level of hydrogen in said treated liquid hydrocarbon stream to about 5 ppm or less.

3. The process of claim 1 wherein said selective hydrogenation unit contains a catalyst selected from the group consisting of reduced forms of Pt, Pd and Ni catalysts.

4. The process of claim 1 wherein said hydrocarbon stream comprises less than about 80 wt % light olefins.

5. The process of claim 1 wherein said light olefins comprise ethylene or propylene.

6. The process of claim 1 wherein sufficient liquid or water vapor is added to said treated liquid hydrocarbon stream so that said gaseous treated hydrocarbon stream has from 50 to 90% humidity when contacting said membrane unit.

7. The process of claim 1 wherein said membrane system comprises a single stage membrane system.

8. The process of claim 1 wherein said membrane system comprises a two stage membrane system wherein a retentate from a first membrane unit is contacted to a second membrane unit to produce a second permeate stream and a second retentate stream.

9. The process of claim 8 wherein said second permeate stream is recycled to said treated liquid hydrocarbon stream or said gaseous treated hydrocarbon stream.

10. The process of claim 1 wherein said membrane system comprises a three stage membrane system wherein a retentate from a first membrane unit is contacted to a second membrane unit to produce a second permeate stream and a second retentate stream and said second retentate stream is sent to a third membrane unit to produce a third permeate stream and a third retentate stream.

11. The process of claim 10 wherein said third permeate stream is combined with said second permeate stream to form a combined stream and wherein said combined stream is recycled to said treated liquid hydrocarbon stream or said gaseous treated hydrocarbon stream.

12. The process of claim 1 wherein said membrane system is operated at a temperature from about 30 to 80° C.

13. The process of claim 1 wherein said gaseous treated hydrocarbon stream is at a pressure from about 80 to about 300 psig before entering the membrane unit.

14. The process of claim 1 wherein said mixture of light olefins and light paraffins comprises propylene and propane, wherein said membrane system comprises a single stage membrane system, and wherein a concentration of propylene in the retentate stream from said single stage membrane system is about 40-45 wt %.

15. The process of claim 1 wherein said mixture of light olefins and light paraffins comprises propylene and propane, and wherein said permeate stream comprises about 99 to 99.5 wt % propylene.

16. The process of claim 1 said mixture of light olefins and light paraffins comprises propylene and propane, and wherein said retentate stream comprises about 7-10 wt % propylene.

* * * * *